(12) United States Patent
Maiefski et al.

(10) Patent No.: US 6,894,777 B2
(45) Date of Patent: May 17, 2005

(54) MULTIPLE-CHANNEL UV SPECTROMETER ASSEMBLY

(76) Inventors: Romaine R. Maiefski, 1312 Hollins Rd., Oceanside, CA (US) 92056; Bruce O. Blizzard, 966 Amber Dr., San Marcos, CA (US) 92069

( * ) Notice: Subject to any disclaimer, the term of this patent is extended or adjusted under 35 U.S.C. 154(b) by 153 days.

(21) Appl. No.: 10/214,869

(22) Filed: Aug. 7, 2002

(65) Prior Publication Data

US 2004/0027568 A1 Feb. 12, 2004

(51) Int. Cl.$^7$ ............................................. G01J 3/28
(52) U.S. Cl. ........................................................ 356/326
(58) Field of Search .............................. 356/326, 328, 356/410–411, 344

(56) References Cited

U.S. PATENT DOCUMENTS

| | | | | |
|---|---|---|---|---|
| 4,519,710 A | * | 5/1985 | Luce et al. | 356/411 |
| 4,685,801 A | * | 8/1987 | Minekane | 356/328 |
| 5,638,171 A | * | 6/1997 | Honig et al. | 356/326 |
| 5,867,266 A | * | 2/1999 | Craighead | 356/344 |
| 6,297,505 B1 | * | 10/2001 | Frandsen et al. | 250/436 |
| 6,404,495 B1 | * | 6/2002 | Melman et al. | 356/344 |
| 2003/0067600 A1 | * | 4/2003 | Curtiss | 356/328 |

FOREIGN PATENT DOCUMENTS

WO   WO 98/20338   * 5/1998   .......... G01N/33/04

* cited by examiner

Primary Examiner—F. L. Evans
Assistant Examiner—Kara Geisel
(74) Attorney, Agent, or Firm—Perkins Coie LLP (57) ABSTRACT

A multiple-channel spectrometer assembly for analyzing a plurality of sample flows. The assembly includes a plurality of spectrometer channels, each fluidly connectable to a respective one of the sample flows. Each channel has a sample inlet and a sample outlet connectable to a respective one of the sample flows. Each channel has a chassis and a light source mounted to the chassis. A spectrometer module is adjacent to each chassis and is optically coupled a light outlet portion of the light source. The spectrometer module has an optical inlet axially coupled to the light outlet portion to receive light from the light source. A high-pressure flow cell assembly is positioned adjacent to the chassis between the light source and the spectrometer module to emulate a fiber optic cable therebetween. The flow cell assembly has a flow passageway in fluid communication with the sample inlet and sample outlet. The flow passageway is configured to receive one of the sample flows therethrough so the light from the light source passes through the sample flow prior to being received by the spectrometer module for analysis of the light absorption profile of the sample.

27 Claims, 8 Drawing Sheets

MULTIPLE-CHANNEL UV SPECTROMETER ASSEMBLY

TECHNICAL FIELD

The present invention is directed to methods and apparatus for spectral analysis, and more particularly to methods and apparatus for ultraviolet and visible light spectral analysis.

BACKGROUND

Collection of thousands, and in some cases millions, of chemical compounds are referred to in the pharmaceutical industry as chemical libraries. Methods have been developed for screening the compounds from a chemical library in an effort to identify, as an example, novel ligands or other the like that can be the basis for a new and effective pharmaceutical drug or the like.

Recently developed synthesis techniques are capable of generating large chemical libraries in a relatively short period of time as compared to previous synthesis techniques. As an example, automated synthesis techniques for sample generation allows for the generation of up to 4,000 or more compounds per week. These samples can include impurities in addition to the desired compound. When samples having these impurities are screened against selected targets, such as a novel ligand or a biological receptor, the impurities can produce erroneous screening results. As a result, samples that receive a positive result from initial screening must be further analyzed and screened to verify the accuracy of the initial screening result. This verification process requires that additional samples be available. The verification process also increases the cost and time required to accurately verify that the targeted compound has been located. Samples can be purified in an effort to achieve an 85% purity or better. Screening of the purified samples provides more accurate and meaningful biological results. Conventional purification techniques, however, are slow and expensive. Conventional purification techniques using high-pressure liquid chromatography (HPLC) take approximately 30 minutes to purify each sample. Therefore, purification of the 4,000 samples generated in one week would take at least 2,000 hours (i.e., 83.3 days or 2.77 months).

There are many different configurations of purification instruments. They typically share commonality in the concept wherein the samples are delivered to a chromatography instrument. The chromatography instrument separates the compounds in time and a fraction collector collects the target compound. A substantial improvement in high throughput purification of samples was developed by Ontogen Corporation of Carlsbad, Calif., U.S.A., which developed a multiple-channel, high throughput supercritical fluid chromatographic purification system. The system is described in U.S. Pat. No. 6,309,541, issued Oct. 30, 2001, which is incorporated herein in its entirety by reference thereto.

The Ontogen purification system simultaneously handles multiple sample flows through the system's multiple purification channels. Each channel uses a stand-alone detector capable of identifying in real time a peak within the sample flow if the peak has selected characteristics. The conventional detectors are UV detectors that identify when a sample with certain absorption characteristics (e.g., a set level of absorption units at selected wavelengths) flowing through the detector. An UV absorption profile for a compound can, however, vary over a range of wavelengths, so some conventional detectors may not detect desired samples with peaks at different absorption wavelengths within the spectrum.

SUMMARY

The present invention provides a multiple-channel spectrometer assembly for simultaneously analyzing a plurality of sample flows. In one embodiment, the single multiple-channel spectrometer assembly can be used for a multiple-channel, high throughput sample handling system, such as a SFC purification system. The multiple-channel spectrometer assembly and related methods overcomes limitations experienced in the prior art and provides additional benefits.

DETAILED DESCRIPTION

The present invention is directed to method and apparatus relating to light-based spectrometer assemblies. In one embodiment, the spectrometer assembly is a multiple-channel assembly for simultaneously analyzing multiple, high-pressure sample flows. The multiple-channel spectrometer assembly has a plurality of spectrometer channels, each fluidly connectable to one of the plurality of sample flows. Each spectrometer channel has a chassis and a light source mounted to the chassis. A spectrometer module is mounted to the chassis and optically coupled to a light outlet portion of the light source. The spectrometer module has an optical inlet optically coupled to the light outlet portion to receive light generated by the light source. A flow cell assembly is adjacent to the chassis between the light source and the spectrometer module to provide a close-coupled light path from the light source to the spectrometer module. The flow cell assembly is configured to emulate a fiber optic cable between the light source and the spectrometer module. The flow cell assembly receives one of the plurality of sample flows through a flow passageway between the light source and spectrometer module, so the light generated from the light source is directed through the sample flow before reaching the spectrometer module. The spectrometer module in each channel is configured to analyze the spectrum of light received from the flow cell assembly and to provide selected data regarding a light absorption profile for compounds in the respective sample flow. A master signal processor is mounted on one of the spectrometer channels and coupled to all of the spectrometer modules and is configured to handle the data from each spectrometer module for all of the sample channels.

In another embodiment, the spectrometer assembly has a spectrometer channel with a light source connected to a spectrometer module by a high-pressure flow cell. The high-pressure flow cell assembly is optically coupled between the light source and the spectrometer module, which are mounted on a channel chassis. The flow cell assembly has a flow cell body that receives a sample flow into a flow passageway through a flow inlet, and the sample flow exits a flow passageway through a flow outlet. The flow cell assembly has first and second optical couplers connected to the flow cell body. The first optical coupler is connected to the light source and directs light from the light source to the second optical coupler. The second optic coupler is connected to the spectrometer module.

The first and second optic couplers have axially aligned portions in the flow cell body with flow-facing ends spaced apart from each other by a selected distance to define a portion of the fluid passageway through the flow cell body. The fluid passageway is free of any unswept dead space as the sample flow moves therethrough. The first optic coupler is configured to direct light across the flow passageway when the high-pressure sample flow passes through the flow passageway. The second optical coupler is configured to receive the spectrum of light from the flow passageway not absorbed by the sample flow and to direct the received light toward the spectrometer module for analysis.

The present invention will be described in detail below with respect to various embodiments and with reference to the Figures. The following description provides specific details for a thorough understanding of, and an enabling description for, these embodiments of the invention. However, one skilled in the art will understand that some embodiments of the invention may be practiced without all of these details. In other instances, well-known structures and functions have not been shown or described in detail to avoid unnecessarily obscuring the description of the embodiments of the invention. The structure and function of the illustrative embodiments of the present invention can best be understood by reference to the figures. The same reference numbers may appear in multiple figures. The reference numbers refer to the same or corresponding structure in those figures.

Figure 1:
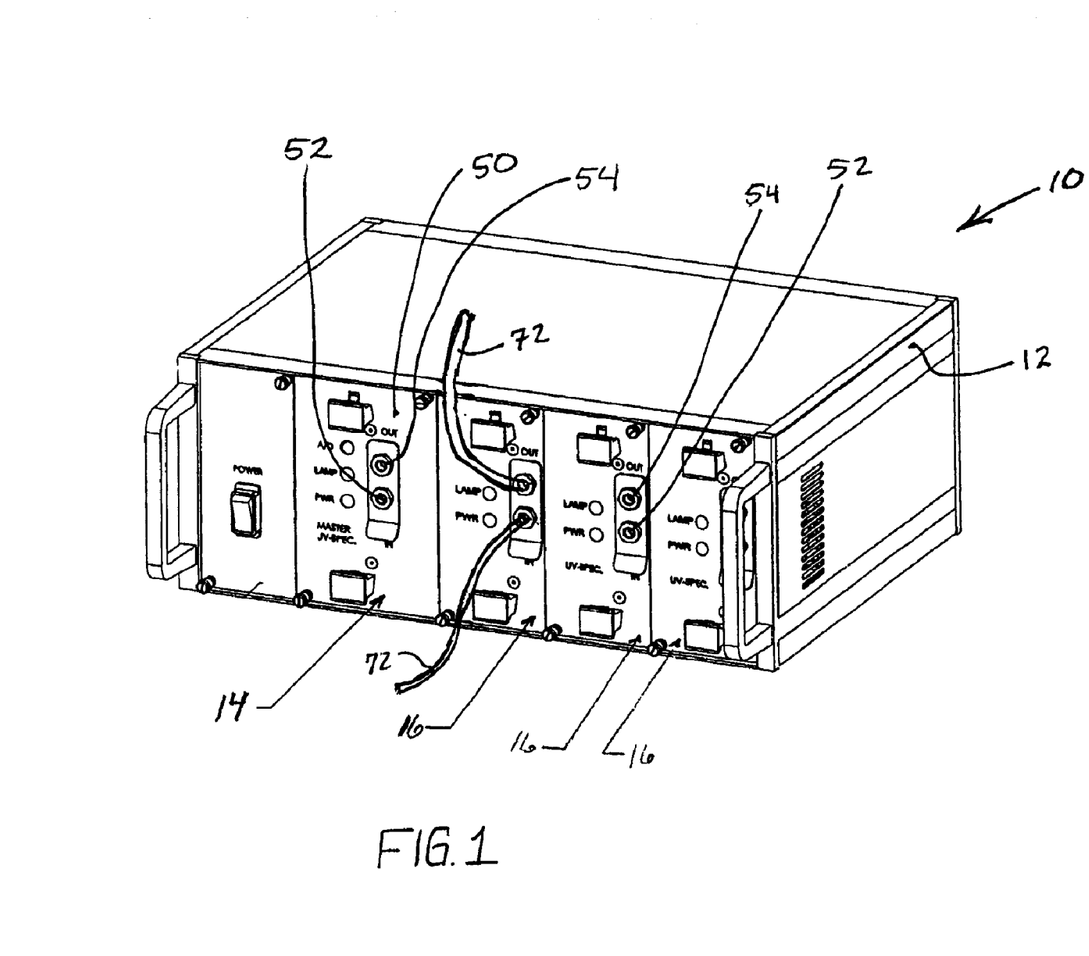
FIG. 1 is an isometric view of a multiple-channel UV spectrometer assembly in accordance with one embodiment of the present invention having a master spectrometer channel and three slave spectrometer channels contained in a first housing.
Figure 2:
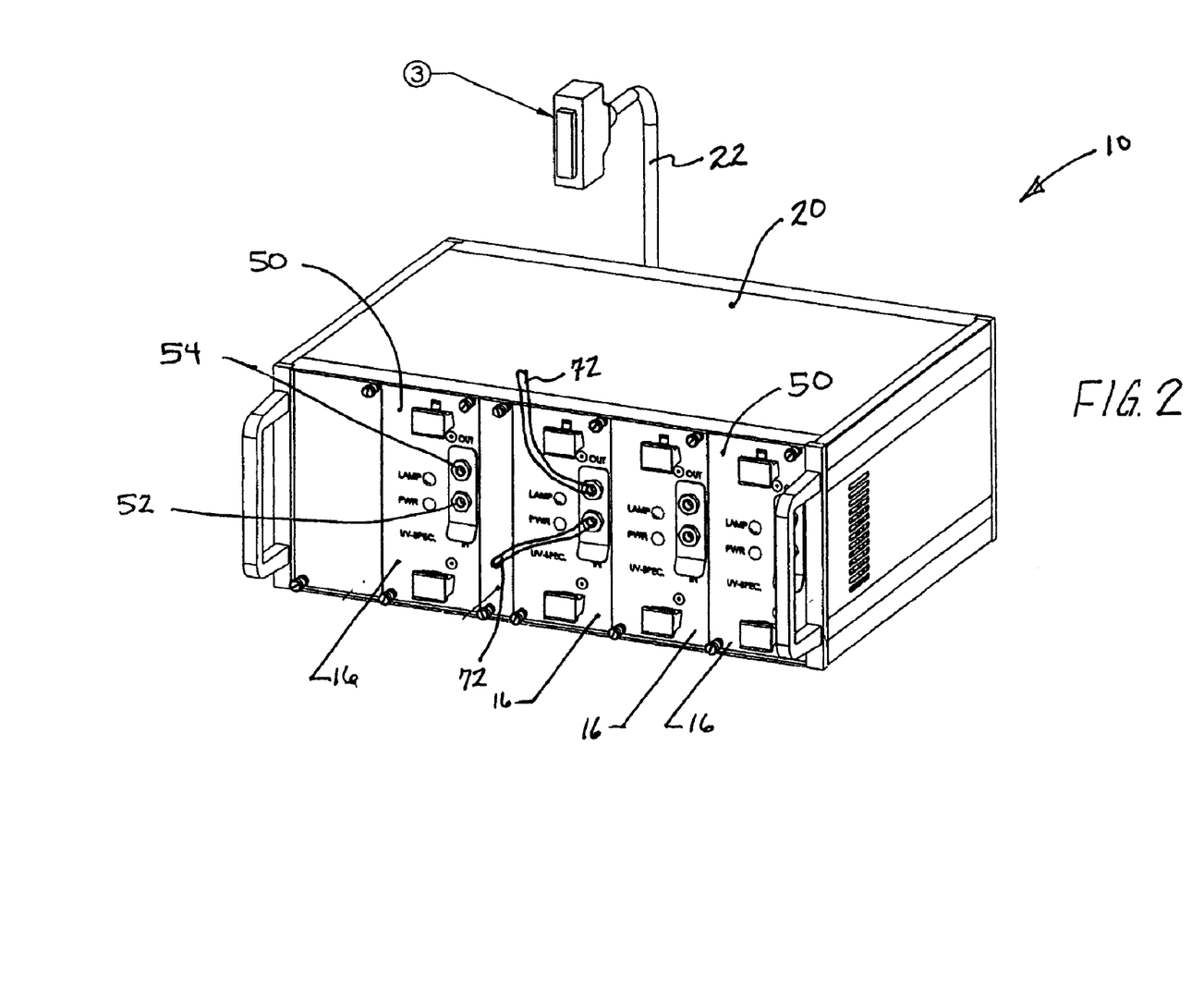
FIG. 2 is an isometric view of a multiple-channel spectrometer assembly with four slave spectrometer channels contained in a second housing and operatively coupled to the master spectrometer channel in the housing of FIG. 1.

FIG. 1 is an isometric view of a multiple-channel spectrometer assembly 10 in accordance with one embodiment of the present invention. The spectrometer assembly 10 of the illustrated embodiment is an Ultra Violet (UV) light spectrometer assembly having a first housing 12 that contains a master spectrometer channel 14 and three slave spectrometer channels 16. Each of the slave channels 16 is operatively coupled to the master channel 14, as discussed in greater detail below, for simultaneous analysis of multiple sample flows. FIG. 2 is an isometric view of a second housing 20 of one embodiment of the multiple-channel spectrometer assembly 10, and the second housing contains four additional slave spectrometer channels 16. Each of the slave channels 16 is operatively connected to the master channel 14 (FIG. 1) by a conventional data bus 22 (FIG. 2).

Figure 3:
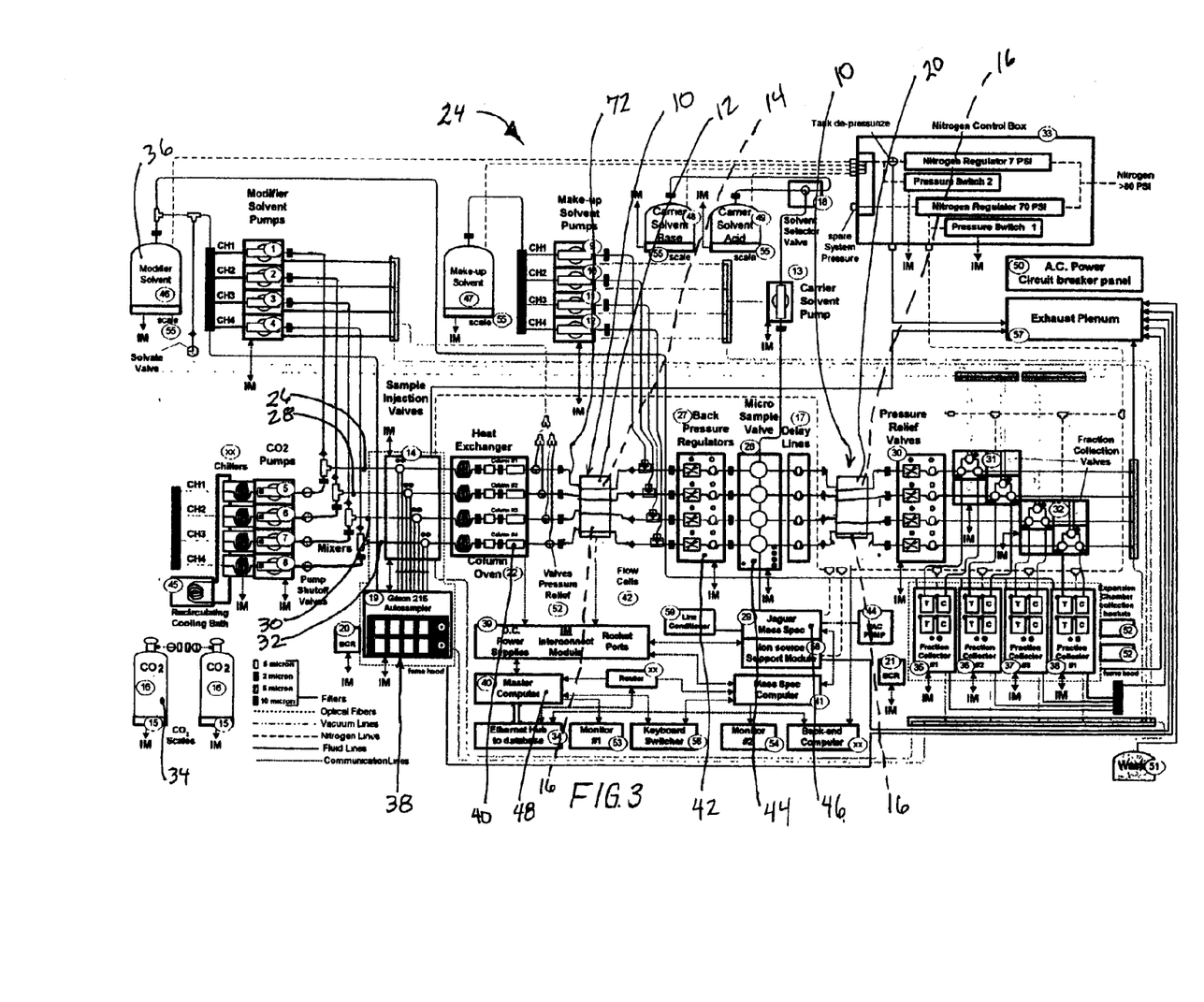
FIG. 3 is a schematic view of a high-throughput sample purification system incorporating the multiple-channel spectrometer assembly at two locations within the system.

Each spectrometer channel 14 and 16 is configured to receive and analyze a selected one of the multiple sample flows. As an example, the multiple-channel spectrometer assembly 10 of the illustrated embodiment is configured to be incorporated in a four-channel, high-throughput sample purification system, such as the OntoCHROMT™ SFC purification system, similar to the system disclosed in U.S. Pat. No. 6,309,541. FIG. 3 is a schematic view of a SFC purification system 150 with the multiple-channel spectrometer assembly 10 incorporated into two places in the system. The purification system 150 is briefly discussed below to provide context for further detailed description of the multiple-channel spectrometer assembly 10.

As best seen in FIG. 3, the illustrated SFC purification system 24 has four sample channels 26, 28, 30, and 32 that are each connected to a source of liquid $CO_2$ 34 and a source of modifier solvent 36, which together form a super-critical carrier fluid. The purification system 24 has an autosampler 38 that automatically introduces selected samples into the carrier fluid in each of the four channels 26, 28, 30, and 32 to provide four simultaneous sample flows in the purification system. Each of the channels 26, 28, 30, and 32 carries its sample flow through a chromatography column 40 so as to separate the components in time along the sample flow through each channel. The first housing 12 of the UV spectrometer assembly 10 is provided just downstream of the chromatography columns 40. The first sample-flow channel 26 is directly connected to the master spectrometer channel 14, and each of the other three sample-flow channels 28, 30, and 32 are connected to one of the three slave spectrometer channels 16 in the first housing 12. Accordingly, the four sample flows are simultaneously passed through the master and slave spectrometer channels 14 and 16 and analyze in real time.

The four sample flows proceed from the master and slave channels 14 and 16 in the first housing 12, through backpressure regulators 42, and through microsample valves 44. Very small portions of selected samples that are identified by the upstream master or slave spectrometer channels 14 or 16 are diverted to a mass spectrometer 46 for additional analysis. The remainder of each sample flow continues downstream from the microsample valves 44 and flows into a respective one of the four slave spectrometer channels 16 in the second housing 20. Each of these downstream slave spectrometer channels 16 analyzes its sample flow and provides spectrometer analysis data back to the master spectrometer channel 14.

The master channel 14 handles all of the data from the slave channels 16 and also provides information to the purification system's master computer 48 to assist in the highly accurate collection of purified compounds for a selected chemical library. Accordingly, the illustrated multiple-channel UV spectrometer assembly 10 provides eight spectrometer channels, so each of the four sample-flow channels 26, 28, 30, and 32 of the purification system 24 include two of the spectrometer channels. In alternate embodiments, the multiple-channel spectrometer assembly 10 can be configured with different numbers of slave channels, and the spectrometer channels can be set up so a sample flow passes through only one or multiple spectrometer channels as is appropriate for the selected sample flow system.

Figure 4:
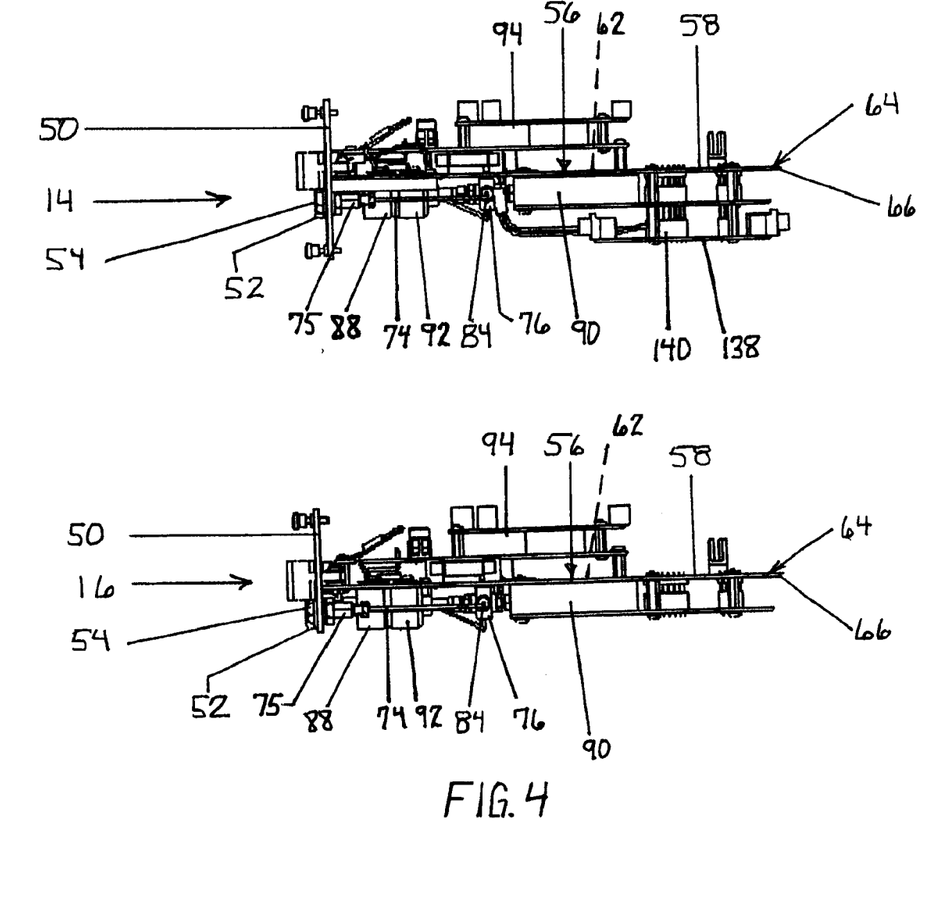
FIG. 4 is an enlarged top plan view of the master channel and one of the slave spectrometer channels shown removed from the first housing of FIG. 1.
Figure 5:
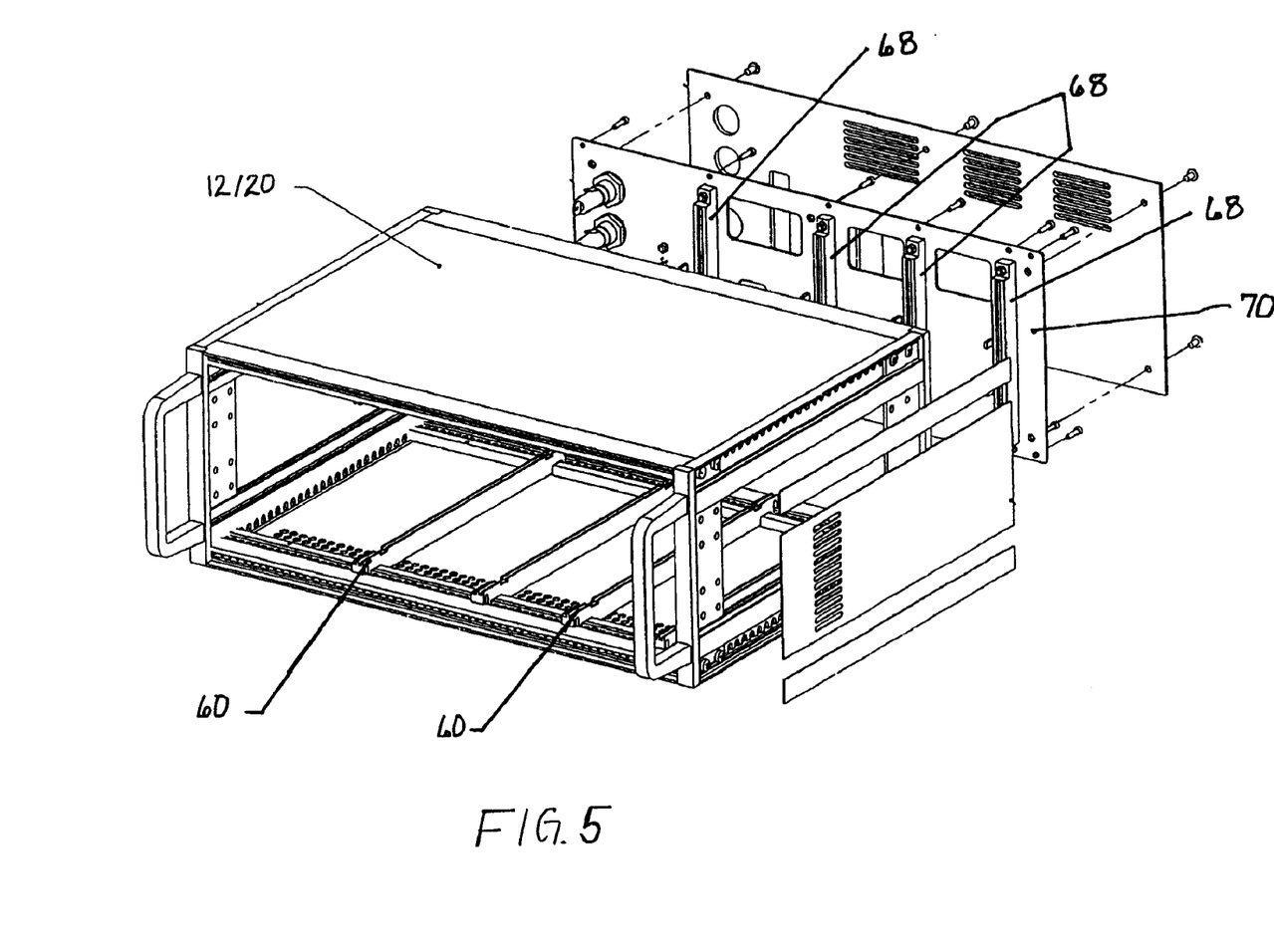
FIG. 5 is a partially exploded isometric view of the first housing of the assembly of FIG. 1, with the master and slave spectrometer channels not shown for purposes of illustration.

FIG. 4 is a top plan view showing the master spectrometer channel 14 and one of the slave channels 16 removed from the housing 12. FIG. 5 is an enlarged, exploded isometric view of the housing 12 of the UV spectrometer assembly 10, with the spectrometer channels removed and not shown for purposes of illustration. As best seen in FIG. 4, each of the master and slave channels 14 and 16 are separate modular units removably contained in one of the housings 12 and 20. Each spectrometer channel 14 and 16 includes a face plate 50 with a flow inlet port 52 and a flow outlet port 54 that connect to the respective sample flow channel of a purification or other multiple-channel system. The face plate 50 is connected to an elongated mounting chassis 56 removably received by the respective housing 12 or 20.

The top and bottom edges 58 of each mounting chassis 56 are adapted to slide into upper and lower receiving rails 60 in the housing 12 or 20, so the mounting chassis is securely supported in a vertical orientation within the housing. The mounting chassis 56 of the illustrated embodiment is an elongated, sturdy printed circuit board securely mounted perpendicular to the face plate. The mounting chassis 56 includes embedded electrical circuitry 62 that electrically interconnects components of each channel as well as other channels as discussed below. In the illustrated embodiment, each of the slave channels 16 in the first and second housings 20 is electrically connected and operatively controlled by the master channel 14. Each of the master and slave channels 14 and 16 receives power from a power source coupled to spectrometer assembly 10.

The rear edge 64 of each mounting chassis 56 has a plurality of electrical connectors 66 electrically coupled to the embedded circuitry 62. The receiving rails 60 align each chassis 56 so that the electrical connectors 66 on the chassis' rear edge 64 plug into an electrical connector 68 mounted to a back wall 70 of the housing 12 or 20. Accordingly, the master channel 14 and slave channels 16 can be easily inserted and plugged into the respective housing 10 or 12, and each channel can be independently removed from the housing while the other channels remain plugged into their respective housing. This modular configuration of the multiple-channel UV spectrometer assembly 10 allows for any downtime of the assembly to be minimized, for example, in the event maintenance or repair of a single spectrometer channel is required, because the affected channel can be quickly removed and replaced with a new spectrometer channel.

Figure 6:
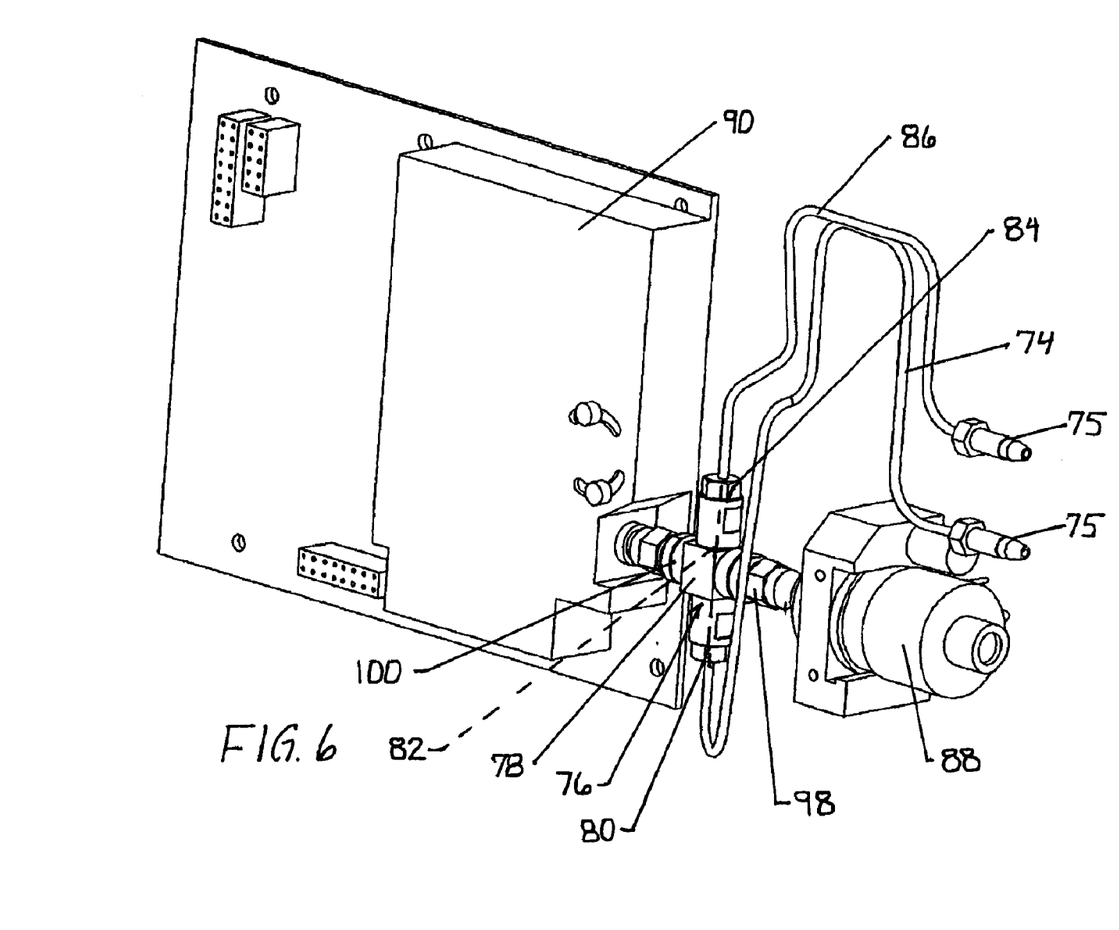
FIG. 6 is an enlarged isometric view of the light source, flow cell assembly, and spectrometer module shown removed from one of the master or slave spectrometer channels.

Each of the master and slave channels 14 and 16 is connected to its respective sample flow line 72 at the flow inlet port 52 (FIG. 4). As best seen in FIG. 6, a small-bore fluid line 74 extends from a fitting 75 that connects to the flow inlet port 52 (FIG. 4). The fluid line 74 is connected to a high-pressure flow cell assembly 76, which includes a flow cell body 78. In one embodiment, the flow cell body 78 is stainless steel, although in other embodiments the flow cell body can be manufactured of other suitable materials to handle the high-pressure flow of the sample therethrough.

The flow cell body 78 receives the sample flow through an inlet 80 connected to a sample passageway 82 extending through the flow cell body. The sample flow exits the flow cell body 78 from the sample passageway 54 through an outlet 84. In the illustrated embodiment, the flow cell's inlet 80 and outlet 84 are coaxially aligned, and the sample passageway 82 is substantially straight through the flow cell body 78. The sample passageway 82 is a small bore passageway suitable for maintaining the high-pressure SFC sample flow in a liquid state while presenting the sample flow for UV or visible light spectral analysis as the sample flow passes through the flow cell body 78. After the sample flow exits the flow cell body 78, another small-bore fluid line 86 carries the sample flow to the flow outlet port 54 (FIGS. 1 and 4) on the face plate 50, and the flow outlet port 54 is removably connected to the sample flow channel of the purification system 24.

The flow cell assembly 76 is connected on one side to a light source 88 and connected on the opposite side to a UV/Vis spectrometer module 90. The flow cell body 78 of the illustrated embodiment is also configured to direct light from the light source 88 through the sample flow moving through the sample passageway 82. The light source 88 is electrically coupled to the circuitry 62 in the mounting chassis 56 (FIG. 4). The light sources 88 on each spectrometer channel 14 and 16 are electrically coupled to a power module 94 mounted to the chassis 56 of the respective channel (FIG. 4). In the illustrated embodiment, the light source 88 is a deutrium lamp that generates ultraviolet light. The deutrium lamp is a low-power light source that stabilizes quickly, which can be particularly advantageous for spectra-analysis of small samples in a flow of supercritical fluid. In an alternate embodiment, the light source 88 can include a tungsten lamp, which provides light in the visible light spectrum. Other light sources 88 can be used in other embodiments to provide measurable light to the flow cell assembly 76 as the fluid sample flows therethrough.

The light source 88 of the illustrated embodiment is releasably attached to the flow cell assembly 76 to provide light into a light inlet port 98 in the flow cell assembly. The light exits the flow cell assembly 76 through a light outlet port 100 after the light passes through the sample flow moving through the flow cell's sample passageway 82. The light from the light outlet port 100 is then directed into the spectrometer module 90 coupled to the flow cell assembly 76 and mounted to the chassis 56 of the respective spectrometer channel 14 or 16 (FIG. 4). Accordingly, the flow cell assembly 76 emulates a fiber optic cable between the light source 88 and the spectrometer module 90.

Figure 7:
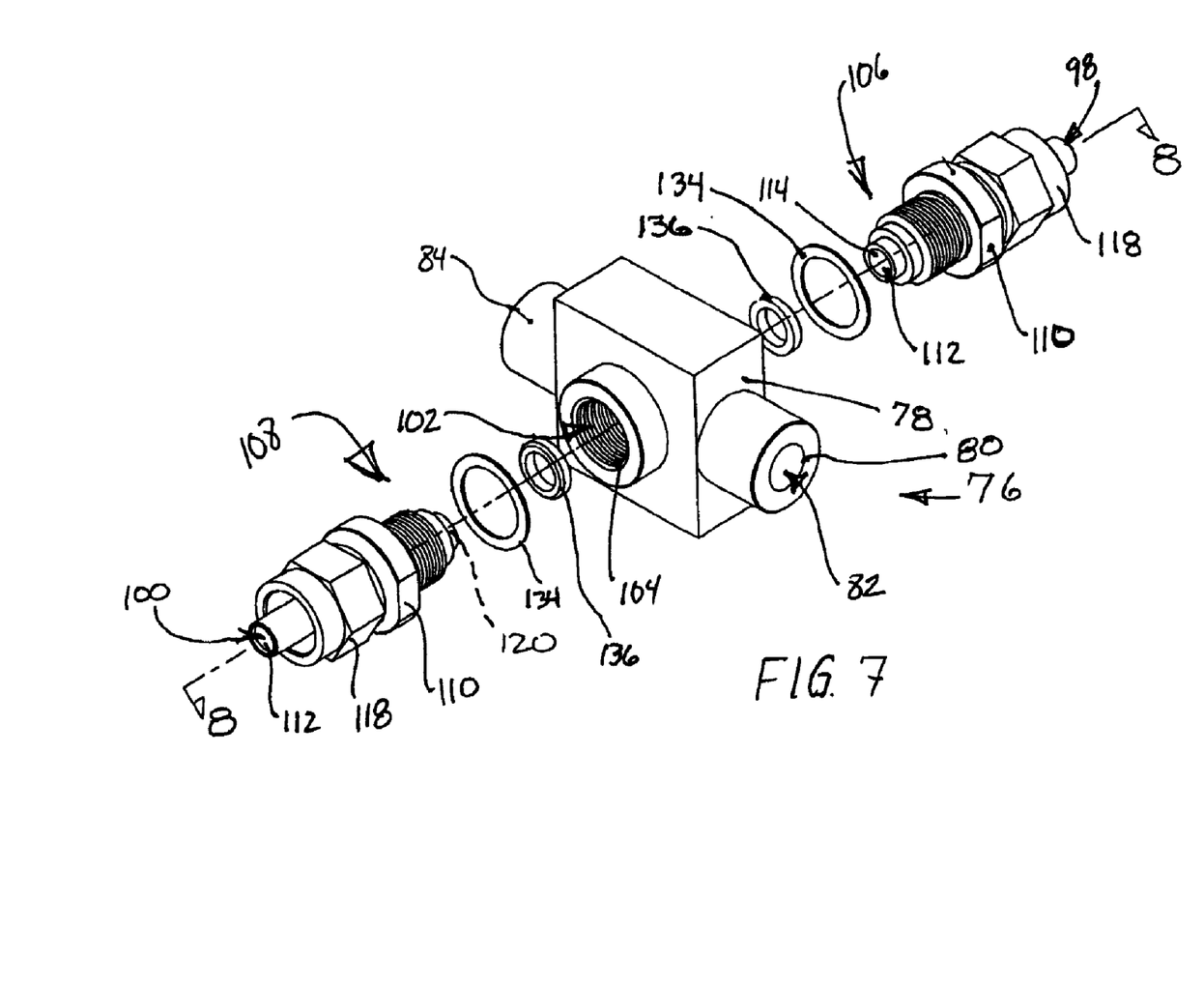
FIG. 7 is an enlarged, exploded isometric view of the flow cell of FIG. 6 shown removed from the channel for purposes of illustration.
Figure 8:
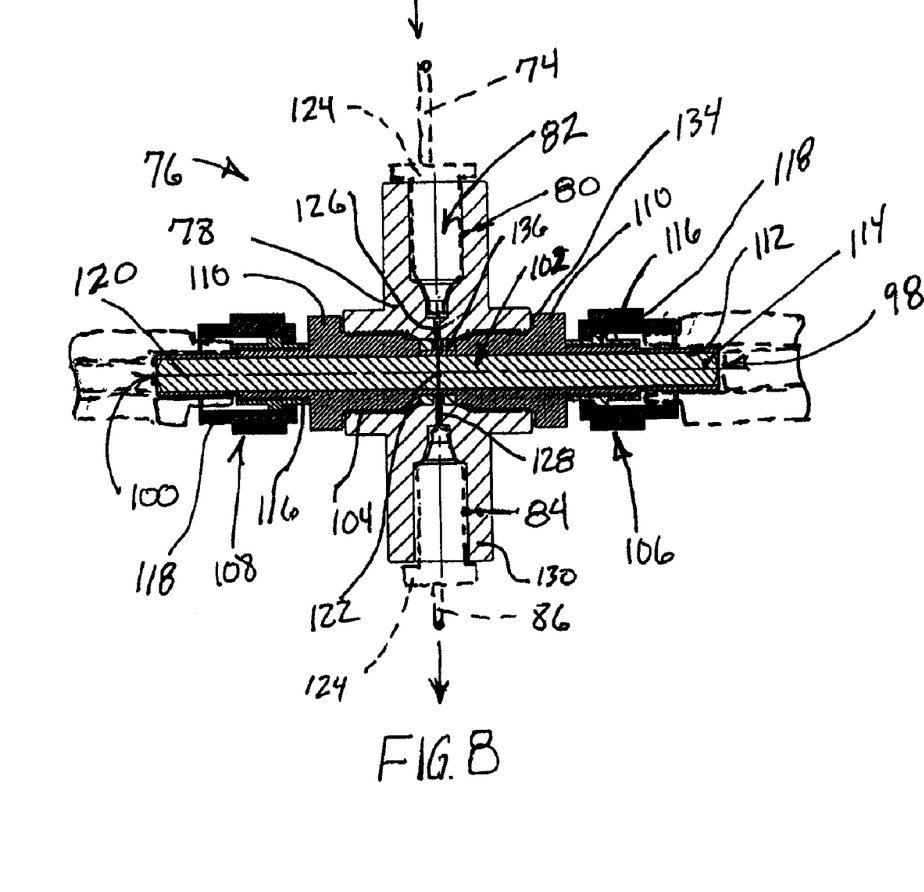
FIG. 8 is an enlarged, cross-sectional view taken substantially along lines 8—8 of FIG. 7.

FIG. 7 is an enlarged exploded isometric view of the flow cell assembly 76 shown isolated for purposes of illustration. FIG. 8 is a cross-sectional view of the flow cell assembly 76 taken substantially along line 8-8 of FIG. 9. The flow cell assembly 76 includes the sample passageway 82 extending through the flow cell body 78 along one axis and a light flow passageway 102 through the flow cell body along a transverse axis. Accordingly, that the sample flow and the light from the light source 88 (FIG. 7) intersect within the flow cell body 78.

The light flow passageway 102 extends through an enlarged bore 104 through the flow cell body 78. The flow cell assembly 76 has an inlet window assembly 106 removably retained in the bore 104 in one end to the flow cell body 78. The inlet window assembly 106 is releasably connected to the light source 88. The flow cell body 78 also has an outlet window assembly 108 removably retained in the other side of the bore 104 opposite the inlet window assembly 106. The outlet window assembly 108 is connectable to the spectrometer module 90 and is configured to direct the light passing through the flow cell body 78 into the spectrometer module for analysis.

As best seen in FIG. 8, the inlet window assembly 106 includes a window housing 110 threadably retained in the bore 104 in the flow cell body 78. The window housing 110 has a central aperture 112 that securely receives an optical window 114 that defines a portion of the light flow passageway 102. In the illustrated embodiment, the optical window 114 is a plano-convex lens. The window housing 110 includes an internally threaded retainer 116 and a retainer collar 118 adapted to releasably connect directly to the optic coupler 96 on the light source 88 (FIG. 7). In an alternate embodiment, the retainer 116 can be connected to a coupler on an optic fiber extending from the light source 88.

The optical window 114 in the inlet window assembly 106 is axially aligned with a corresponding optical window 120 in the outlet window assembly 108. The outlet window assembly 108 has substantially an identical configuration as an inlet window assembly 106 discussed above. The ends of the optical windows 114 and 120 are flat surfaces spaced apart from each other by a selected distance to define a gap 122 that forms a portion of the sample passageway 82 through the flow cell body 78. Accordingly, when the high-pressure sample flow passes through the flow cell body 78, the sample flow passes through the gap 122 between the flat ends of the optical windows 114 and 120. The optical windows 114 and 120 are configured to efficiently direct light from the inlet optical coupler 106, across the gap 122 into the optical outlet coupler 108 and into the UV spectrometer module 90.

The sample passageway 82 through the flow cell body 78 is connected to the sample inlet 80 that releasably and sealably connects to a fitting 124 on the channel's small bore fluid line 74, as shown in FIG. 9. The sample inlet 80 has a small-bore inlet channel 126 in fluid communication with the gap 137 axially aligned with the inlet channel 126. The inlet bore channel 126 directs the high-pressure sample flow through the gap 122 perpendicularly across the light flow passageway 102 and between the flat ends of the optical windows 114 and 120. The sample flow exits the gap 122 into a small-bore outlet channel 128 opposite the inlet channel 126. The outlet channel 128 is in fluid communication with a sample outlet 130, which removably receives a fitting 132 on the fluid line 74 connected to the channel's outlet port 54.

As the sample flow moves through the fluid passageway 82 between the optical windows 114 and 120 and substantially perpendicular to the light, the sample flow absorbs portions of the light spectrum, and the remaining light is received by the spectrometer module 90. The portion of the fluid passageway 82 extending between the inlet and outlet window assemblies 106 and 108 provides substantially zero dead space and no unswept volume in the flow cell body 78, thereby minimizing the risk of any cross-contamination between samples flowing through the flow cell body. Also, the width of the portion of the fluid passageway 82 between the inlet and window assemblies 106 and 108 can be adjusted by changing the distance between the optical windows 114 and 120.

In the illustrated embodiment, the flow cell assembly 76 includes a washer 134 sandwiched between each window housing 110 and the flow cell body 78. The width of the fluid passageway 82 can be modified by using washers 134 of different thicknesses. The flow cell assembly 76 also includes a seal 136 having a chamfered surface that engages the end of each window housing 110 and sealably engages the flow cell body 78. The seals 136 prevent any migration of the sample flow past the flat ends of the inlet and outlet window assemblies 106 and 108 as the sample is moving through the fluid passageway 82.

The high-pressure flow cell assembly 76 of the illustrated embodiment is provided in direct contact with the light source and the spectrometer module, so as to provide a close-coupled light path between the UV light source 88 and the spectrometer module 90. Thus, the sample flow in each fluid channel 26, 28, 30, or 32 (FIG. 3) is delivered to the respective master or slave spectrometer channel 14 or 16 and through the flow cell assembly 76. The sample flow also passes through the light from the light source 88 on the respective spectrometer channel 14 or 16, and the sample's UV absorption profile is analyzed by the spectrometer module 90. The spectrometer module 90 receives the spectrum of light that has passed through the sample flow in the flow cell assembly 76 without being absorbed and analyzes that portion of the light. The spectrometer module 90 on each of the master and slave channels 14 and 16 is operatively connected to the circuitry 62 on the mounting chassis 56 to receive power from the channel's power module 94. In the illustrated embodiment, the spectrometer module 90 is a module manufactured by Ocean Optics, Inc., of Dunedin, Fla. and configured to provide a UV absorption profile for the sample along a range of wavelengths from approximately 190 to 700 nanometers.

Each spectrometer module 90 of the illustrated embodiment is configured to simultaneously provide an analysis of the full spectrum to determine a broad UV absorption profile for each sample flow. Obtaining this broad UV absorption profile allows for a very accurate determination of the peaks in the sample and the scope of absorption across a range of wavelengths by the particular sample flowing through the sample flow cell assembly 76.

All of the spectrometer modules 90 are connected to only one signal processor 138 piggybacked on the mounting chassis 56 of the master spectrometer channel 14. Accordingly, the slave channels 16 do not require an on-board signal processor thereby reducing the cost and complexity of each slave channel. The slave channels 16 do, however, have an identifier that provides a signal to the signal processor 138 that identifies which position each slave channel is in within the first or second housings 12 or 20 (FIGS. 1 and 2). Accordingly, the signal processor 138 can match the data from each spectrometer module 90 with the sample flow channel to which the spectrometer channel is attached.

The signal processor 138 in the illustrated embodiment includes an integral analog-to-digital converter 140 coupled to the circuitry 62 in the chassis 56 of the master channel 14. The analog-to-digital converter 140 receives the analog data from each spectrometer module 90 and converts the data into a digital format. The signal processor 138 also includes an onboard central processing unit that can be selectively programmed to utilize selected portions of the absorption profile to control subsequent processing of the sample flow. As an example, one embodiment includes a signal processor 138 programmed to focus on ten selected sets of wavelengths, wherein each set spans approximately 9 nanometers. If a change in UV spectral transmittance is detected within one or more of the sets, the absorption profile may be analyzed in greater detail to determine whether the sample is a target sample that is to be collected from the sample flow. In addition to data regarding a sample's UV absorption profile, the signal processor 138 also receives data in real time regarding the timing of the sample passing through the respective flow cell assembly 76. The signal processor 138 is also configured to provide data about each of the sample flows to the master computer 48 for the purification system 24. This allows the master computer to monitor the precise location of each detected sample within the flow channel for subsequent processing and purification.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

We claim:

1. A multiple-channel spectrometer assembly for analyzing a plurality of sample flows, comprising:

a plurality of spectrometer channels each being fluidly connectable to a respective one of the plurality of sample flows, each channel having:

a sample inlet and a sample outlet connectable to a respective one of the sample flows;

a chassis;

a light source having a light outlet portion;

a spectrometer module mounted to the chassis and optically aligned with the light source, the spectrometer module having an optical inlet axially aligned with the light outlet portion of the light source; and a flow cell assembly adjacent to the chassis intermediate the light source and the spectrometer module, the flow cell having a flow passageway in fluid communication with the sample inlet and sample outlet and configured to receive one of the plurality of sample flows therethrough, the flow passageway being positioned between the light source and the spectrometer, the flow cell assembly being configured to direct light from the light source toward the spectrometer module as the sample flow moves through the flow passageway; and a signal processor coupled to each of the spectrometer modules and configured to receive data from each spectrometer module.

2. The spectrometer assembly of claim 1 further comprising a housing, and the plurality of the spectrometer channels are contained in the housing.

3. The spectrometer assembly of claim 1 further comprising a single power module coupled to each of the plurality of spectrometer channels and to the signal processor.

4. The spectrometer assembly of claim 1 wherein the signal processor includes an analog-to-digital converter.

5. The spectrometer assembly of claim 1 wherein the plurality of spectrometer channels includes a master spectrometer channel with the signal processor connected thereto, and a plurality of subsidiary channels separate from the master channel and the signal processor.

6. The spectrometer assembly of claim 1, further comprising a first housing that contains the signal processor and a first set of the plurality of the spectrometer channels, and a second housing that contains a second set of the plurality spectrometer channels, the second housing being independent of the first housing and each spectrometer channel in the second set is operatively coupled to the signal processor in the first housing.

7. The spectrometer assembly of claim 1 wherein the flow cell assembly is a high-pressure flow cell configured to receive a high-pressure fluid sample flow therethrough.

8. The spectrometer assembly of claim 1 wherein each flow cell assembly includes a flow cell body having a sample passageway extending therethrough and in fluid communication with the sample inlet and sample outlet, the flow cell assembly emulating a fiber optic connection between the light source and the spectrometer module of the respective spectrometer channel.

9. The spectrometer assembly of claim 1 wherein each of the flow cell assemblies includes:

a flow cell body mounted to the respective chassis, the flow cell body having a sample flow inlet, a sample flow outlet, and a sample passageway extending therebetween, the sample flow inlet being in fluid communication with the sample inlet, and the sample flow outlet being in fluid communication with the sample outlet; and first and second light couplers removably connected to the flow cell body, first light coupler being positioned in axial alignment with the light outlet portion of the light source and the second light coupler positioned in axial alignment with the optical inlet of the spectrometer module.

10. The spectrometer assembly of claim 9 where the first light coupler has:

a first connector releasably connected to the light outlet portion of the light source and connected to the flow cell body, a first flow cell window connected to the first connector, the first flow cell window having a light receiving end and a light outlet end, the light receiving end being positioned adjacent to the light outlet portion of the light source to receive light from the light source and the light outlet end being positioned within the flow cell body adjacent to the sample passageway to direct light across the sample flow passageway, and the second light coupler has:

a second connector releasably connected to the respective spectrometer module and connected to the flow cell body;

a second flow cell window connected to the second connector, the second flow cell window having a light receiving end and a light outlet end, the light receiving end being positioned in the flow cell body and spaced apart from the light outlet end of the first flow cell window on an opposite side of the sample passageway, the second flow cell window being in axial alignment with the first flow cell window and with the optical inlet of the spectrometer module.

11. The spectrometer assembly of claim 1 wherein each flow cell assembly includes optical connectors interconnecting the flow cell assembly to the light source and to the spectrometer module on the respective chassis.

12. The spectrometer assembly of claim 1 wherein light source is an ultra violet light source.

13. The spectrometer assembly of claim 1 wherein the light source contains a Deuterium lamp and a tungsten lamp.

14. The spectrometer assembly of claim 1 wherein the plurality of the spectrometer channels includes a primary spectrometer channel and a plurality of secondary spectrometer channels, the primary spectrometer channel having a first chassis, and the signal processor is connected to the first chassis, and further comprising a power module connected to the first chassis and coupled to the signal processor and spectrometer module.

15. The spectrometer assembly of claim 1, wherein the signal processor includes an analog-to-digital converter coupled to each of the spectrometer channels.

16. A multiple-channel UV spectrometer assembly for analyzing a plurality of liquid sample flows, comprising:

a plurality of spectrometer channels each being fluidly connectable to a respective one of the plurality of liquid sample flows, each channel having:

a sample inlet and a sample outlet connectable to a respective one of the liquid sample flows;

a chassis;

a light source having a light outlet portion;

a spectrometer module mounted to the chassis and having an optical inlet optically coupled to the light outlet portion to receive light from the light source; and a high-pressure flow cell assembly coupled between the light source and the spectrometer module for transferring light therebetween, the flow cell assembly having a sample flow passageway in fluid communication with the sample inlet and sample outlet and configured to receive one of the plurality of sample flows therethrough, the sample flow passageway positioned between the light source and the spectrometer and configured to receive light generated from the light source before the light is received by the spectrometer module; and a signal processor coupled to each of the spectrometer modules and configured to receive data from each spectrometer module.

17. The spectrometer assembly of claim 16 wherein each spectrometer channel includes connectors interconnecting the high-pressure flow cell assembly to the respective light source and to the respective spectrometer module.

18. A multiple-channel spectrometer assembly for analyzing a plurality of simultaneous sample flows, comprising:

a first housing;

a primary spectrometer channel positioned in the first housing and being connectable to one of the sample flows, the primary spectrometer channel having a sample inlet and a sample outlet;

a first chassis;

a first light source having a first light outlet portion;

a first spectrometer module mounted to the first chassis and optically aligned with the first light source, the first spectrometer module having an optical inlet axially aligned with the first light outlet portion to receive light from the first light source; and a first flow cell assembly adjacent to the first chassis intermediate the first light source and the first spectrometer module, the first flow cell assembly having a first flow passageway in fluid communication with the sample inlet and sample outlet and configured to receive one of the plurality of sample flows therethrough, the first flow passageway being positioned between the first light source and the first spectrometer module and configured to receive light generated from the first light source and directed toward the first spectrometer module as the sample flow moves through the first flow passageway; and a signal processor coupled to the first spectrometer module and configured to receive data from the first spectrometer module;

a first set of secondary spectrometer channels positioned in the first housing;

a second housing;

a second set of secondary spectrometer channels positioned in the second housing;

each of the secondary spectrometer channels in the first and second housings having:

a second chassis;

a second light source having a second light outlet portion;

a second spectrometer module mounted to the second chassis and coupled to the signal processor in the first housing, each second spectrometer module being optically aligned with the second light source, the second spectrometer module having an optical inlet coupled to the second light outlet portion to receive light from the second light source; and a second flow cell assembly adjacent to the second chassis intermediate the second light source and the second spectrometer module, the second flow cell assembly having a second flow passageway in fluid communication with the sample inlet and sample outlet and configured to receive one of the plurality of sample flows therethrough, the second flow passageway being positioned between the second light source and the second spectrometer module and configured to receive light generated from the second light source and directed toward the second spectrometer module as the sample flow moves through the second flow passageway.

19. The spectrometer assembly of claim 18 wherein each of the primary and secondary spectrometer channels includes a power module coupled to the first or second light source.

20. The spectrometer assembly of claim 18 wherein the signal processor includes an analog-to-digital converter.

21. The spectrometer assembly of claim 18 wherein each of the first and second flow cell assemblies is a high-pressure flow cell assembly configured to receive a high-pressure fluid sample flow therethrough.

22. The spectrometer assembly of claim 18 wherein the first flow cell assembly includes a flow cell body mounted to the first chassis, the flow cell body having the first flow passageway therethrough and in fluid communication with the sample inlet and sample outlet, the first flow cell assembly having a close-coupled light path intersecting the first flow passageway and extending between the first light source and the first spectrometer module.

23. The spectrometer assembly of claim 18 wherein the first flow cell assembly includes:

a flow cell body mounted to the first chassis, the flow cell body having a sample flow inlet, a sample flow outlet, and the first flow passageway extending therebetween, the sample flow inlet being in fluid communication with the sample inlet, and the sample flow outlet being in fluid communication with the sample outlet;

first and second light couplers removably connected to the flow cell body, first light coupler being positioned in axial alignment with the light outlet portion of the light source and the second light coupler positioned in axial alignment with the optical inlet of the first spectrometer module.

24. The spectrometer assembly of claim 23 where the first light coupler has:

a first connector releasably connected to the light outlet portion of the light source and connected to the flow cell body;

a first flow cell window connected to the first connector, the first flow cell window having a light receiving end and a light outlet end, the light receiving end being positioned adjacent to the light outlet portion of the light source to receive light from the light source and the light outlet end being positioned within the flow cell body adjacent to the sample passageway to direct light across the first flow passageway; and the second light coupler has:

a second connector releasably connected to the respective spectrometer module and connected to the flow cell body;

a second flow cell window connected to the second connector, the second flow cell window having a light receiving end and a light outlet end, the light receiving end being positioned in the flow cell body and spaced apart from the light outlet end of the first flow cell window on an opposite side of the sample passageway, the second flow cell window being in axial alignment with the first flow cell window and with the optical inlet of the spectrometer module.

25. A multiple-channel spectrometer assembly for analyzing a plurality of sample flows, comprising:

a plurality of spectrometer channels each being fluidly connectable to a respective one of the plurality of sample flows, each channel having:

a sample inlet and a sample outlet connectable to a respective one of the sample flows;

a chassis;

a light source having a light outlet portion;

a spectrometer module mounted to the chassis and optically aligned with the light source, the spectrometer module having an optical inlet axially aligned with the light outlet portion of the light source; and a flow cell assembly intermediate the light source and the spectrometer module, the flow cell having a flow passageway in fluid communication with the sample inlet and sample outlet and configured to receive one of the plurality of sample flows therethrough, the flow passageway being positioned between the light source and the spectrometer and configured to emulate a fiber optic cable therebetween to direct light from the light source toward the spectrometer module as the sample flow moves through the flow passageway.

26. A spectrometer assembly for analyzing a high-pressure sample flow, comprising:

a light source having a light outlet portion; a spectrometer module having an optical inlet configured to receive light from the light source: and a high-pressure flow cell assembly optically coupled between the light source and the spectrometer module, the flow cell assembly having a flow cell body with a flow inlet configured to receive the sample flow, and a flow outlet in fluid communication with the flow inlet, the flow cell assembly having first and second optical couplers connected to the flow cell body, the first optical coupler being coupled to the light source and the second optical coupler being connected to the spectrometer module, the first and second optical couplers having axially aligned portions in the flow cell body with flow-facing ends spaced apart from each other by a selected distance to define a fluid passageway therebetween in fluid communication with the flow inlet and flow outlet, the fluid passageway being free of upswept dead space while the sample flow moves therethrough, the first optical coupler is configured to direct light across the flow passageway when the high-pressure sample flow passes through the flow passageway, and the second optical coupler is configured to receive light from the flow passageway and directed toward the spectrometer module, wherein the first and second couplers are axially moveable relative to the flow cell body and to each other.

27. A spectrometer assembly for analyzing a high-pressure sample flow, comprising:

a light source having a light outlet portion; a spectrometer module having an optical inlet configured to receive light from the light source; and a high-pressure flow cell assembly optically coupled between the light source and the spectrometer module, the flow cell assembly having a flow cell body with a flow inlet configured to receive the sample flow, and a flow outlet in fluid communication with the flow inlet, the flow cell assembly having first and second optical couplers connected to the flow cell body, the first optical coupler being coupled to the light source and the second optical coupler being connected to the spectrometer module, the first and second optical couplers having axially aligned portions in the flow cell body with flow-facing ends spaced apart from each other by a selected distance to define a fluid passageway therebetween in fluid communication with the flow inlet and flow outlet, the fluid passageway being free of upswept dead space while the sample flow moves therethrough, the first optical coupler is configured to direct light across the flow passageway when the high-pressure sample flow passes through the flow passageway, and the second optical coupler is configured to receive light from the flow passageway and directed toward the spectrometer module, wherein the first and second couplers are each threadably connected to the flow cell body and axially adjustable to adjust the size of the flow passageway.

* * * * *